US00PP16551P2

(12) United States Plant Patent
Trees

(10) Patent No.: US PP16,551 P2
(45) Date of Patent: May 16, 2006

(54) HELIOTROPE PLANT NAMED 'BALHELBABIM'

(50) Latin Name: *Heliotropium arborescens*
Varietal Denomination: Balhelbabim

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 59 days.

(21) Appl. No.: 11/015,397

(22) Filed: Dec. 17, 2004

(51) Int. Cl.
*A01H 5/00* (2006.01)

(52) U.S. Cl. ..... Plt./226
(58) Field of Classification Search ..... Plt./226
See application file for complete search history.

*Primary Examiner*—Anne Marie Grunberg
(74) *Attorney, Agent, or Firm*—Wood, Phillips, Katz, Clark & Mortimer

(57) ABSTRACT

A new and distinct cultivar of Heliotrope plant named 'Balhelbabim', characterized by its light purple-colored flowers, medium green-colored foliage, and compact and upright growth habit.

1 Drawing Sheet

Latin name of the genus and species of plant claimed: *Heliotropium arborescens.*
Variety denomination: 'Balhelbabim'.

BACKGROUND OF THE INVENTION

The present invention comprises a new and distinct cultivar of Heliotrope plant botanically known as *Heliotropium arborescens* and hereinafter referred to by the cultivar name 'Balhelbabim'.

The new cultivar originated in a controlled environment during October 2000 at Arroyo Grande, Calif. The objective of the breeding program was the development of Heliotrope cultivars with a compact and upright growth habit and freely branching character.

The new cultivar is the result of self-pollination, of the cultivar 'Mini Marine', not patented, characterized by purple-colored flowers, upright growth habit, and medium-green-colored foliage. The new cultivar was discovered and selected by the inventor as a single flowering plant within the progeny of the above stated open-pollination during January 2001 in a controlled environment at Arroyo Grande, Calif.

Asexual reproduction of the new cultivar by terminal stem cuttings since 2001 at Arroyo Grande, Calif. and West Chicago, Ill., has demonstrated that the new cultivar reproduces true to type with all the characteristics, as herein described, firmly fixed and retained through successive generations of such asexual propagation.

SUMMARY OF THE INVENTION

The new cultivar has not been observed under all possible environmental conditions to date. Accordingly, it is possible that the phenotype may vary somewhat with variations in the environment, such as temperature, light intensity, and day length without, however, any variance in genotype.

The following characteristics of the new cultivar have been repeatedly observed and can be used to distinguish 'Balhelbabim' as a new and distinct cultivar of Heliotrope plant:

1. Light purple-colored flowers.
2. Medium green-colored foliage.
3. Compact and upright growth habit.

Of the Heliotrope cultivars known to the inventor, the most similar to the new cultivar is 'Mini Marine'. However, in side by side comparisons, plants of the new cultivar differ from plants of 'Mini Marine' in the following characteristics:

1. Plants of the new cultivar are wider than plants of 'Mini Marine'.
2. Plants of the new cultivar have branches having a smaller diameter than plants of 'Mini Marine'.
3. Plants of the new cultivar have shorter internodes than the plants of 'Mini Marine'.
4. Plants of the new cultivar have a more heavily branching habit than plants of 'Mini Marine'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which more accurately describe the colors of 'Balhelbabim'. The plants were grown in 10 cm pots for 10 weeks in a greenhouse at West Chicago, Ill.

DETAILED BOTANICAL DESCRIPTION

Figure 1:
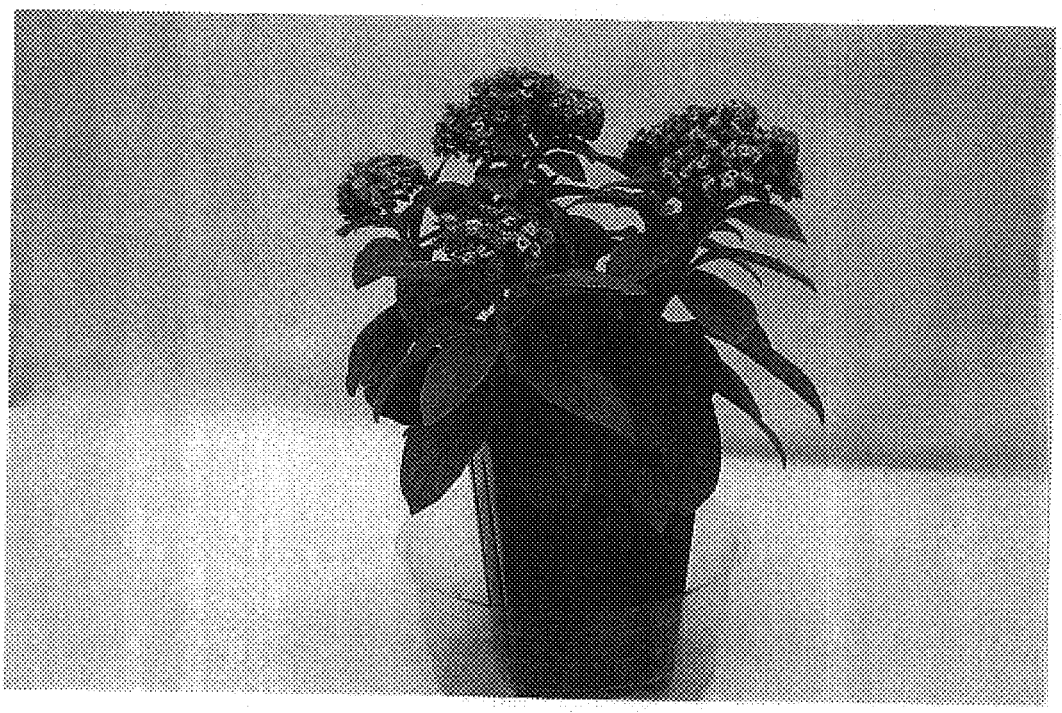
FIG. 1 illustrates the overall growth habit of the new cultivar with one plant per pot.
Figure 2:
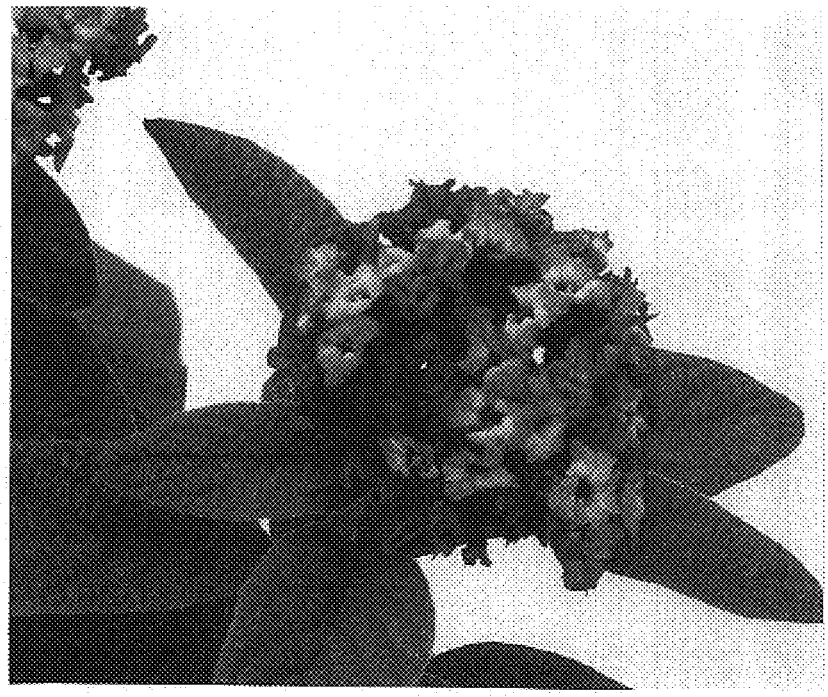
FIG. 2 illustrates a close up view of flowers and foliage of the new cultivar.

The chart used in the identification of colors described herein is The R.H.S. Colour Chart of The Royal Horticultural Society, London, England, 2001 edition, except where general color terms of ordinary significance are used. The color values were determined on Nov. 5, 2004 in West Chicago, Ill., between 1:00 and 3:00 p.m. under natural light conditions.

The following descriptions and measurements describe plants produced from cuttings taken from stock plants and grown in a double polycarbonate-covered greenhouse under conditions comparable to those used in commercial practice. The plants were grown in 10 cm pots for 12 weeks utilizing a soil-less growth medium. Greenhouse temperatures were maintained at approximately 70° to 75° F. (21° to 24° C.) during the day and approximately 50° to 60° F. (10° to 15° C.) during the night. Light levels were maintained at approximately 5,000 to 9,000 footcandles during the day.

Botanical classification: *Heliotropium arborescens* cultivar Belhelbabim.

Parentage:

*Open pollination*.—Female parent being the commercially available *Heliotropium arborescens* cultivar Mini Marine, not patented.

Propagation:

*Type cutting*.—Terminal tip.

*Time to initiate roots*.—Approximately 8 to 10 days.

*Time to produce a rooted cutting*.—Approximately 14 to 21 days.

*Root description*.—Fibrous.

*Rooting habit*.—Freely branching.

Plant description:

*Crop time*.—6–7 weeks.

*Growth habit*.—Compact, upright. One or two pinches improve branching.

*Form*.—Upright.

*Size*.—Height from soil level to top of plant plane: Approximately 14.4 cm. Diameter (area of spread): Approximately 26.2 cm.

*Lateral flowering branches*.—Quantity: an average of 4 per plant. Length: Approximately 12 cm. Diameter: Approximately 3 mm. Texture: Densely pubescent. Color: 146C. Internode length at middle of branch: Approximately 6 mm.

*Foliage*.—Quantity: Approximately 15 per branch. Fragrance: None. Type: Simple. Arrangement: Alternate. Shape: Elliptic. Margin: Entire. Apex: Acute. Base: Attenuate. Venation pattern: Pinnate. Length: Approximately 7 cm. Width: Approximately 3 cm. Texture: Upper and lower surfaces are densely covered with short, soft hairs. Color: Upper surface of mature foliage is 137A with venation of N144B. Lower surface of mature foliage is 137B with venation of N144B. Petiole length: Approximately 4 mm. Petiole diameter: Approximately 1.3 mm. Petiole texture: Densely pubescent with short, soft hairs. Petiole color: 144B.

Flowering description:

*Flowering habit*.—Freely flowering under outdoor growing conditions with substantially continuous blooming from spring through autumn and year round in greenhouse environment.

Inflorescence description:

*Type*.—Terminal compound cymes.

*Size*.—Height: Approximately 3.5 cm. Width: 5 cm. Quantity of open flowers per inflorescence: Approximately 23.

*Peduncle*.—Strength: Strong. Aspect: At an acute angle to the stem. Length: Approximately 1.8 cm. Diameter: Approximately 1.3 mm. Texture: Densely pubescence. Color: 146C.

Flower description:

*Flower type*.—Funnelform. Flowers are persistent.

*Bud*.—Shape: Tubular. Length: Approximately 4 mm. Diameter: Approximately 2 mm. Color: N87B.

*Flower size*.—Length: Approximately 6 mm. Corolla diameter: Approximately 7 mm.

*Petals*.—Quantity: Five, fused at base forming tube. Apex: Rounded. Margin: Entire. Texture: Upper surface: Glabrous. Lower surface: Glabrous except for moderate pubescence along mid-vein. Color when first open: Upper surface: N87A. Lower surface: N87C. Color when fully open: Upper surface: N87C with 155C at base of petals around corolla tube opening. Lower surface: N87D.

*Corolla tube*.—Length: 4.5 mm. Diameter at base: 1.8 mm. Diameter at tube opening: 2.4 mm. Texture of outer surface: Densely pubescent. Texture of inner surface: Glabrous. Color of outer surface: 146D and base of 155C. Color of inner surface: 145B.

*Calyx*.—Diameter: Approximately 2 mm. Sepal quantity: Five, fused at base. Shape: Linear. Length: Approximately 4 mm. Width: Approximately 2 mm at base. Apex: Acute to acuminate. Margin: Entire. Texture: Outer/lower surface is densely pubescent with long soft hairs. Inner/upper surface is moderately pubescent with short soft hairs. Color: Both surfaces are 146B.

*Reproductive organs*.—Androecium: There are 5 stamens fused to inside of tube. Length of free portion of stamen: Approximately 2 mm. Anther shape: Arrow. Anther length: Approximately 1.5 mm. Anther color: N199D. Amount of pollen: Abundant. Pollen color: Lighter than 4D. Gynoecium: Pistil quantity: One. Length: Approximately 1.7 mm. Stigma shape: Thimble. Stigma length: Less than 0.7 mm. Stigma color: 150D. Style length: Less than 0.4 mm. Style color: 150D. Ovary diameter: 0.6 mm. Ovary color: 144B.

Seed and fruit production: Neither seed nor fruit production has been observed.

Disease and pest resistance: Resistance to pathogens and pests common to Heliotrope has not been observed.

What is claimed is:

1. A new and distinct cultivar of Heliotrope plant named 'Balhelbabim', substantially as herein shown and described.

* * * * *